United States Patent [19]

Cabral

[11] Patent Number: 5,311,881
[45] Date of Patent: May 17, 1994

[54] LOAD SENSING AND MEASURING SYSTEM

[76] Inventor: Louis Cabral, Rte. 8, Box 327, Fayetteville, Tenn. 37334

[21] Appl. No.: 11,239

[22] Filed: Jan. 29, 1993

[51] Int. Cl.$^5$ .................................................. A61B 5/103
[52] U.S. Cl. ......................................... 128/782; 73/302
[58] Field of Search .................. 128/774, 782; 73/302, 73/305, 306

[56] References Cited

U.S. PATENT DOCUMENTS

| | | | |
|---|---|---|---|
| 4,474,063 | 10/1984 | Krueger | 73/302 |
| 4,592,371 | 6/1986 | Pellicano et al. | 128/774 |
| 4,949,729 | 8/1990 | Haski | 128/782 |

FOREIGN PATENT DOCUMENTS 3221115  12/1983  Fed. Rep. of Germany ...... 128/782

*Primary Examiner*—Max Hindenburg
*Attorney, Agent, or Firm*—E. Michael Combs

[57] ABSTRACT

A system for sensing and measuring the forces acting on the body extremities of individuals is disclosed. The system is intended for use primarily in an aqueous medium, i.e. as an aquatic dynamometer, and includes a pressure indicator for measuring the dynamic forces acting on the body extremities of individuals during their movement in water. The pressure indicator is positioned on a float situated on the surface of the water. An attachment element is mounted on the pressure indicator to detachably connect the indicator and the float to a wall or other fixed part of a water-containing vessel and in a fixed position on the water surface. Alternatively, the pressure indicator may be secured to a mounting plate. An attachment element comprising a pair of gripping plates extending from the mounting plate are configured to detachably grip a stationary portion of the vessel. One or more load cells for sensing the dynamic forces are connected to the pressure indicator. One or more straps are mountable on the body extremities, and the straps are provided with connecting means for detachably joining to the straps to the load cells in the aqueous medium. The system has another intended use for measuring the buoyancy of body extremities, i.e. the static forces acting thereon while floating on or immersed in water, as well as a tertiary use for measuring the static forces acting on those extremities on land, i.e. their weights.

15 Claims, 4 Drawing Sheets

LOAD SENSING AND MEASURING SYSTEM

BACKGROUND OF THE INVENTION

1. Field of the Invention

The field of the invention relates to load sensing and measuring systems, and more particularly to an apparatus for sensing and quantitatively measuring the forces exerted on the body extremities of individuals.

2. Description of the Prior Art

Exercise programs designed for use in an aqueous medium are commonly practiced for a wide variety of different purposes. For example, exercise in water is used in physical or occupational therapy for rehabilitation from sports or other injuries, as well as in training programs to maximize the physical conditioning of professional athletes or those other persons (i.e. amateurs) interested in maintaining a desired level of physical fitness. However, use of these programs, i.e. simply exercising in water for rehabilitation or general physical conditioning without objective monitoring of the performed movements, fail to provide a precise indication or measurement of progress to determine the overall effectiveness of a particular program.

Various load sensing and measuring systems have been utilized in the prior art. For example, U.S. Pat. No. 3,005,337 to El Waziri sets forth a load cell having a flexible diaphragm and a plurality of concentric bearing rings positioned on the diaphragm for measuring loads induced by elements of varying dimensions acting on the bearing rings.

U.S. Pat. No. 3,248.937 to Vincent discloses a system for measuring loads in an aqueous medium using load sensors and measuring gauges.

U.S. Pat. No. 4,474,063 to Krueger illustrates a system for measuring the weight of bulk material in a storage tank using a load cell with a flexible diaphragm (in the bottom of the tank) in fluid connection with a pressure gauge for measuring the weight of the material therein.

As such, it may be appreciated that there continues to be a need for a new and improved load sensing and measuring system which addresses both the problems of ease of use, portability, and effectiveness in construction, and in this respect, the present invention fulfills this need.

SUMMARY OF THE INVENTION

In view of the foregoing disadvantages inherent in the known types of load sensing and measuring systems now present in the prior art, the present invention provides a system for sensing and quantitatively measuring the forces acting on the body extremities of individuals. As such, the general purpose of the present invention, which will be described subsequently in greater detail, is to provide a new and improved load sensing and measuring system which has all the advantages of the prior art load sensing and measuring systems and none of the disadvantages.

The present invention is primarily intended for use in an aqueous medium, i.e. as an aquatic dynamometer, and includes a pressure indicator for measuring the dynamic forces acting on the body extremities of individuals during their movement in water. The pressure indicator is positioned on a float situated on the surface of the water. An attachment element is mounted on the pressure indicator to detachably connect the indicator and the float to a wall or other fixed part of a water-containing vessel and in a fixed position on the water surface. Alternatively, the pressure indicator may be secured to a mounting plate. An attachment element comprising a pair of gripping plates extending from the mounting plate are configured to detachably grip a stationary portion of the water-containing vessel which is dimensioned to be received between the gripping plates. One or more load cells for sensing the dynamic forces are connected to the pressure indicator. One or more straps are mountable on the body extremities, and the straps are provided with connecting means for detachably joining the straps to the load cells in the aqueous medium. Another intended use of the load sensing and measuring system of the present invention is the measurement of the buoyancy of body extremities, i.e. the static forces acting thereon while floating on or immersed in water, while a tertiary use thereof is the measurement of the static forces acting on those extremities on land, i.e. their weights.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the included abstract is to enable the U.S. Patent and Trademark Office and the public generally, and especially the scientists, engineers, and practitioners in the art who are not familiar with patent or legal terms or phraseology, to determine quickly from a cursory inspection, the nature and essence of the technical disclosure of the application. The abstract is neither intended to define the invention of the application, which is measured by the claims, nor is it intended to be limiting as to the scope of the invention in any way.

It is therefore an object of the invention to provide a new and improved load sensing and measuring system which has all the advantages of the prior art load sensing and measuring systems and none of the disadvantages.

It is another object of the present invention to provide a new and improved load sensing and measuring system which may be easily and efficiently manufactured and marketed.

It is a further object of the present invention to provide a new and improved load sensing and measuring system which is of durable and reliable construction.

An even further object of the present invention is to provide a new and improved load sensing and measuring system which is susceptible of a low cost of manufacture with regard to both materials and labor, and which accordingly is then susceptible of low prices of sale to the consuming public, thereby making such load sensing and measuring systems economically available to the buying public.

Still yet another object of the present invention is to provide a new and improved load sensing and measuring system which provides in the apparatuses and methods of the prior art some of the advantages thereof, while simultaneously overcoming some of the disadvantages normally associated therewith.

Still another object of the present invention is to provide a new and improved load sensing and measuring system which enables quantitative measurements of the forces exerted on the extremities of individuals during their movement in water in order to provide a more precise measure of their effectiveness to achieve a desired result, to provide an accurate means to adjust the movements to obtain those results, and to facilitate the formulation of more varied and beneficial treatments and training routines.

Yet another object of the present invention is to provide a new and improved load sensing and measuring system for quantitatively measuring the forces exerted on the extremities of individuals during their movement in water in order to provide objective base data against which future data can be compared to effect a more precise determination of progress.

A further object of the present invention is to provide a new and improved load sensing and measuring system for quantitatively measuring buoyancy, i.e. the static forces acting on body extremities immersed in or floating upon the water, as well as the static forces acting on those extremities on land, i.e. their weights.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
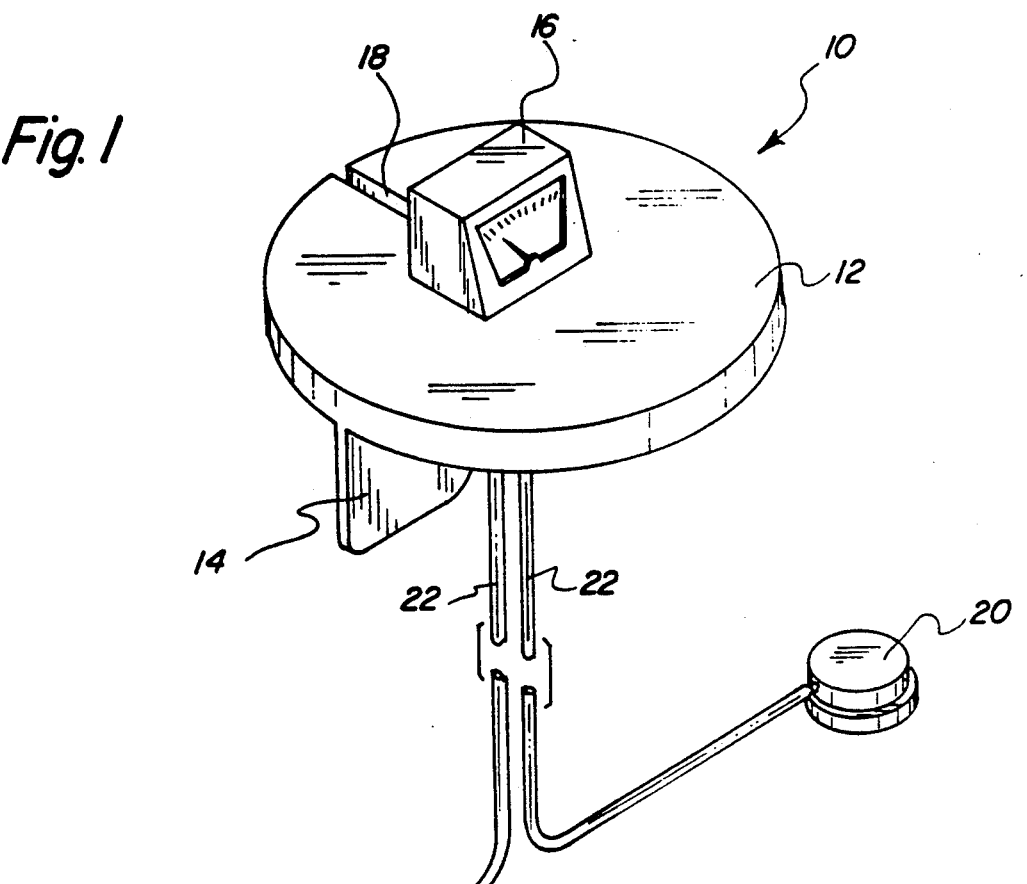
FIG. 1 is a perspective view of the load sensing and measuring system of the present invention.
Figure 2:
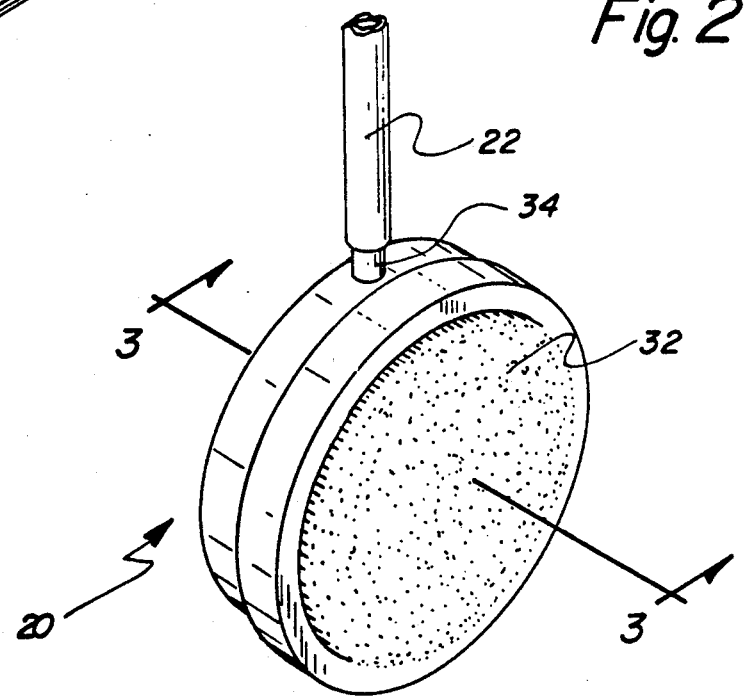
FIG. 2 is a perspective view of the load cell of the present invention.

With reference now to the drawings, and in particular to FIGS. 1-10 thereof, a new and improved load sensing and measuring system 10 embodying the principles and concepts of the present invention and generally designated by the reference numeral 10 will be described.

Figure 4:
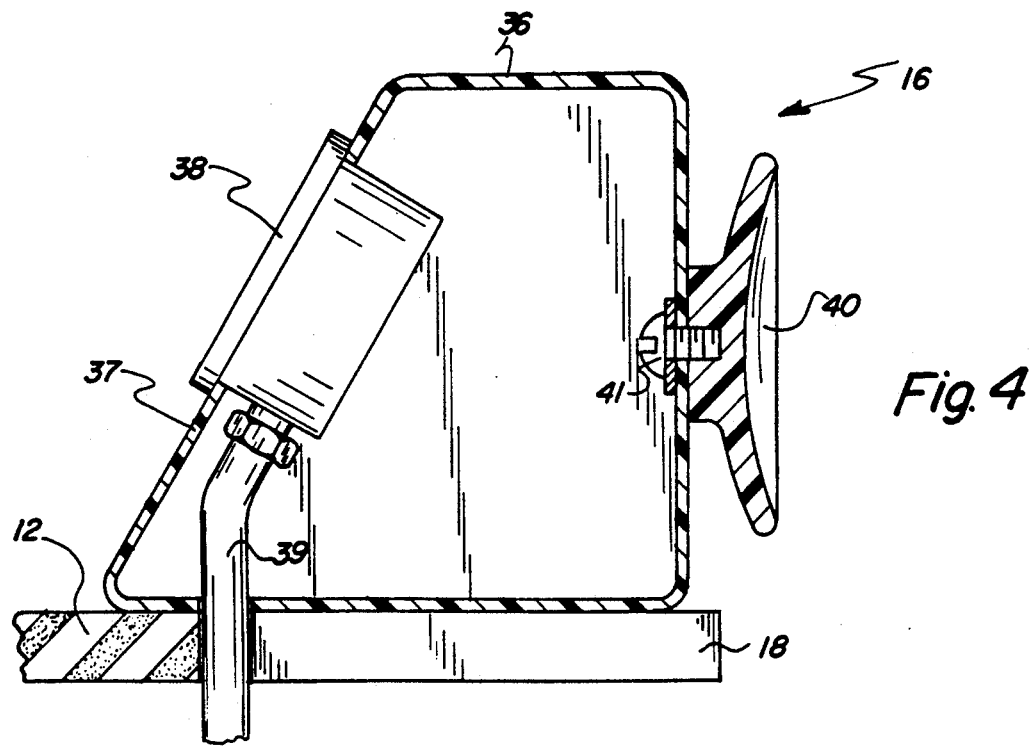
FIG. 4 is a cross-sectional view of the pressure indicator of the present invention.
Figure 7:
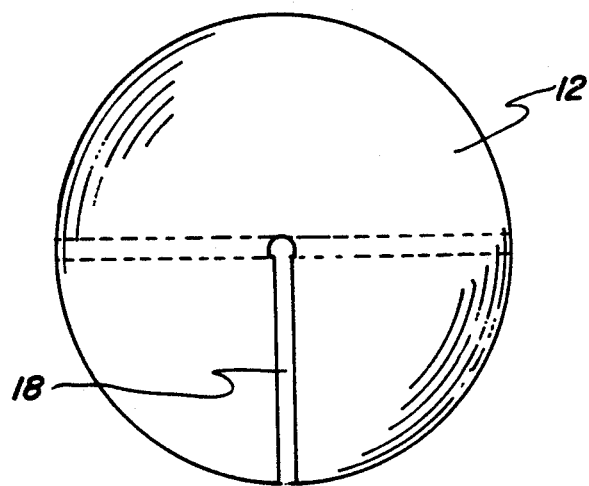
FIG. 7 is a top plan view of the float of the present invention.
Figure 8:
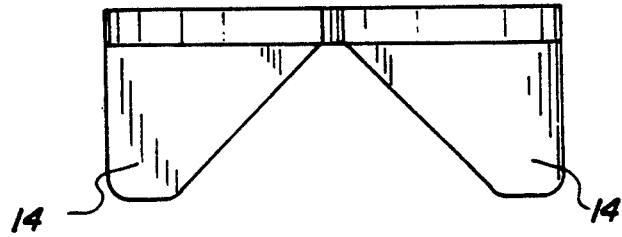
FIG. 8 is front view of the float of the present invention.

More specifically, and with particular reference to FIG. 1, the load sensing and measuring system 10 of the present invention essentially comprises a disc-shaped support or float 12 which may be constructed of polymeric material such as Styrofoam ®. Extending downwardly from the underside of float 12 are a pair of opposed stabilizing fins 14 which are integrally formed with float 12 and also constructed of polymeric material. Stabilizing fins 14 have a truncated triangular shape and extend substantially diametrically across the underside of float 12 as shown in FIGS. 7 and 8. A pressure indicator 16 is detachably mounted on a center portion of the upper surface of float 12 using conventional fasteners (not shown). Pressure indicator 16 is also mounted on float 12 in a manner wherein it partially overlies an access slot 18 which is provided through float 12 (FIGS. 1 and 4). Access slot 18 extends radially from the center to the periphery of float 12, and is arranged orthogonally to stabilizing fins 14 as illustrated in FIGS. 7 and 8. A plurality of load cells 20 are connected to pressure indicator 16 by flexible tubes 22, preferably rubber, which are filled with pressurizing fluid. Only two load cells 20 are shown in FIG. 1 for purposes of clarity of illustration only; any desired number of load cells may be used.

Figure 3:
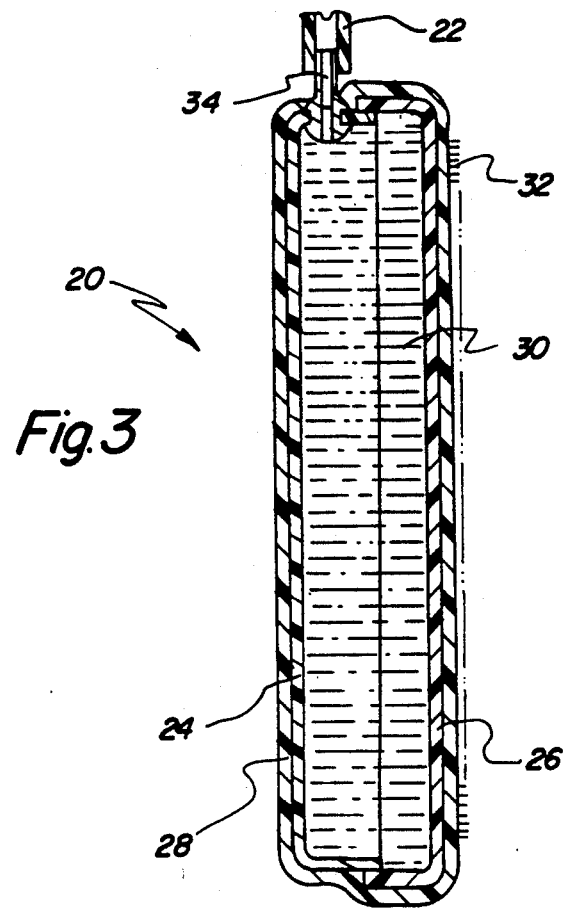
FIG. 3 is a cross-sectional view of the load cell of the present invention taken along line 3—3 in FIG. 2.

Referring now to FIG. 3, the specific structure of load cells 20 will be described. Load cell 20 includes a first cup-shaped member 24 slidably mounted within a larger second cup-shaped member 26. Members 24 and 26 may be constructed of polymeric material. Surrounding members 24 and 26 in a contacting manner is a flexible outer casing 28 which maintains members 24 and 26 in a sealed and telescoping assembled relationship. The chamber defined by the inner cavities of the nested members 24 and 26 provides a fluid reservoir 30 which is filled with pressurizing fluid under vacuum. Casing 28 may be constructed of rubber. Secured to the outer end surface of casing 28 adjacent member 26 is a patch of Velcro ® backing material 32. Mounted on the periphery of member 24 is a stem 34 which extends through the wall of member 24 and into reservoir 30 at one end thereof. Stem 34 is sealingly secured to the flexible tube 22 at the opposite end thereof to complete the closed hydraulic circuit between load cell 20 and pressure indicator 16.

As illustrated in FIG. 4, pressure indicator 16 comprises a housing 36 of polymeric material. The conventional fasteners (not shown) used to mount pressure indicator 16 on float 12 extend between housing 36 and float 12. Mounted on an angled forward wall 37 of housing 36 is a pressure gauge 38. Connected to pressure gauge 38 are a plurality of rigid metal pipes 39 (only one is shown) which are filled with pressurizing fluid and extend downwardly through the bottom wall of housing 36 and float access slot 18 to a position below float 12 where they are sealingly connected to the ends of tubes 22. With this construction, pressure indicator 16 is easily removed from float 12 for replacement or repair by loosening or removing the noted fasteners and sliding indicator 16, and pipes 39, tubes 22, and load cells attached thereto, along the upper surface of float 12 and access slot 18 until those elements are removed from said upper surface and slot 18. Mounted on a rear wall of housing 36 is a suction cup 40 constructed of flexible polymeric material. Mounting of suction cup 40 on the rear wall is effected by means of a conventional fastener 41.

Figure 5:
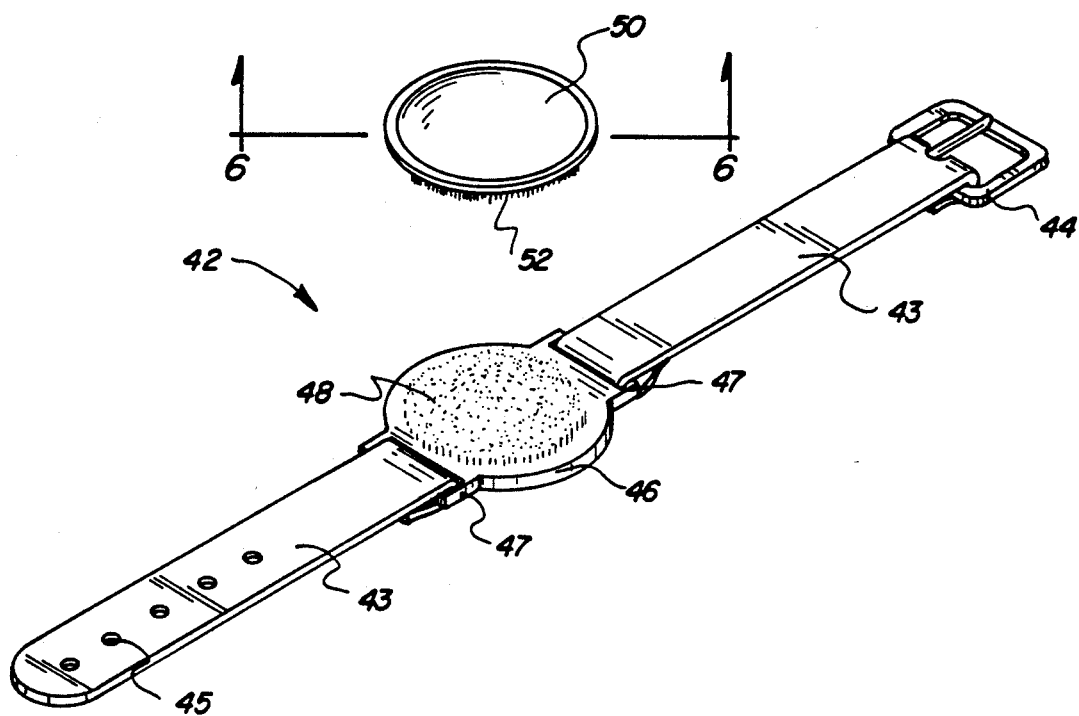
FIG. 5 is a perspective view of the body extremity attachment means of the present invention.
Figure 6:
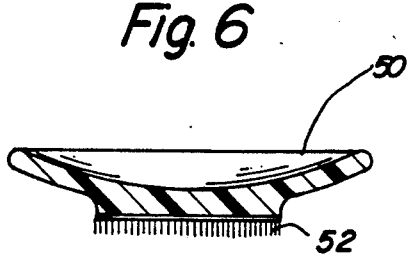
FIG. 6 is a cross-sectional view of the suction cup of the body extremity attachment means of the present invention taken along line 6—6 of FIG. 5.

FIGS. 5 and 6 show a body extremity attachment means 42 which comprises a strap assembly which includes a pair of elongate straps 43. Straps 43 may be formed of flexible polymeric fabric material. One of the straps 43 has a plurality of holes 45 at one end thereof and a closed loop at the opposite end thereof. The other strap 43 has a buckle 44 at one end and a closed loop at its opposite end. The closed loop of each strap 43 is secured to a respective mounting element 47 integrally formed on the periphery of a disc-shaped plate 46. Mounting elements 47 are formed at diametrically positions on plate 46. Secured to a planar surface of plate 46 is a circular patch of Velcro® backing material 48. Detachably secured to patch 48 and plate 46 of the strap assembly is a flexible suction cup 50 made of polymeric material. Secured to a rear surface of cup 50 is a circular patch of Velcro® backing material 52. Accordingly, patches 48 and 52 provide the detachable connection between suction cup 50 and attachment means 42.

Figure 10:
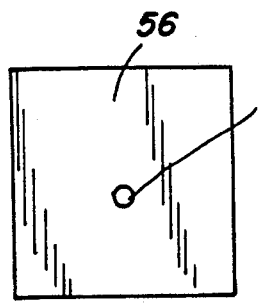
FIG. 10 is a rear end view of the alternative gauge support and attachment means of the present invention as viewed in the direction of line 10—10 in FIG. 9.
Figure 9:
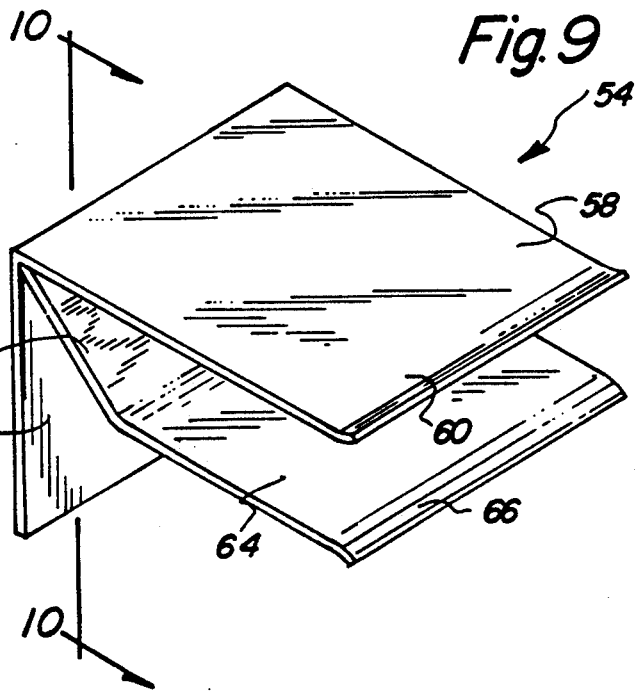
FIG. 9 is a perspective view of an alternative gauge support and attachment means of the present invention.

With reference to FIGS. 9 and 10, a gauge support and attachment means 54 is illustrated. The gauge support means comprises a mounting plate 56 with a centrally positioned hole 57 extending therethrough for receiving a plug of material such as cork or rubber therein(not shown). Extending orthogonally from one planar surface of plate 56 is the attachment means which comprises a first gripping plate 58 having an upwardly curved outer end portion 60 and a second gripping plate having a downwardly angled first section 62, a second gripping section 64 extending from first section 62 and arranged parallel to first plate 58, and a downwardly curved outer end portion 66 which is aligned with the upwardly curved outer end portion of first gripping plate 58. Gauge support and attachment means 54 may be constructed of flexible polymeric material.

In use, float 12 and pressure indicator 16 thereon are first detachably secured to a wall or other fixed part of a water-containing vessel and in a fixed position on the surface of the water in the vessel by pressing suction cup 40 (mounted on the rear wall of pressure indicator housing 36) against the wall or fixed part of the water vessel. Alternatively, pressure indicator 16 may be secured in the water vessel by forcibly pressing flexible gripping plate 58 and gripping section 64 of the second plate of the attachment means into engagement with a fixed portion of the water vessel which is dimensioned to be received between gripping plate 58 and gripping section 64. For example, the vessel portion may be a portion of the vessel wall surrounding an opening therein such as a pool skimmer. The joinder of the attachment means with the vessel portion is facilitated by the curved outer ends 60 and 66 of gripping plate 58 and gripping section 64, respectively, and the attachment means is maintained in detachable assembly with the vessel portion by the spring action of the forcibly separated gripping plate 58 and gripping section 64. Pressure indicator 16 is then detachably secured to gauge support and attachment means 54 by pressing suction cup 40 against mounting plate 56 in surrounding relationship with hole 57 and the plug therein. The noted plug facilitates the disengagement of suction cup 40 and plate 56. Alternatively, pressure indicator 16 and gauge support and attachment means 54 may be joined first and then that assembly may then be joined with the vessel portion. Next, one or more attaching means 42 are secured to the body extremities of an individual positioned in the water vessel by looping straps 43 around the extremity and engaging buckle 44 with a selected hole 45. Each attaching means 42 is then detachably connected to a load cell 20 by pressing Velcro® patch 48 on plate 46 of attaching means 42 against Velcro® patch 32 on an outer end surface of casing 28 of load cell 20. Alternatively, attaching means 42 may be detachably connected to each load cell 20 by pressing Velcro® patch 52 into engagement with Velcro® patch 48 and the pressing suction cup 50 against the same outer end surface of casing 28 which has the Velcro® patch 32 removed therefrom. With the body extremities connected to the load cells 20 as described, the extremities are moved in the water. This movement is resisted by the water in the tank creating a force which acts on load cell sections 24 and 26 and thus pressurizes the fluid in reservoir 30. This pressure created in load cells 20 is measured and indicated by pressure gauge 38 which is hydraulically connected to the load cells 20 by tubes 22 and pipes 39.

Alternatively, after one or more body extremities have been connected to load cells 20 as described in the preceding paragraph, the extremities are held stationary in the water, either immersed therein or floating on the surface. In this manner, the buoyancy of the extremities, i.e. the static forces of the water acting thereon, may be sensed by load cells 20 and measured and indicated by pressure gauge 38. Further, stationary body extremities may also be connected to load cells 20 wherein the body extremities and the sensing and measuring system 10 are positioned on land for measuring the static forces acting thereon, i.e. the weights of the extremities.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function, and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A system for sensing and measuring forces acting on a body extremity comprising:

a pressure indicator;
support means;
first fastener means for detachably mounting said pressure indicator on said support means;
first attachment means for detachably securing said pressure indicator and said support means to a stationary portion of a water-containing vessel;
pressure sensing means;
connecting means for hydraulically joining said sensing means to said pressure indicator; and
second attachment means detachably mountable on said body extremity for detachably connecting said pressure sensing means to said second attachment means and said body extremity;
whereby when said body extremity is positioned in and held stationary in said water contained in said vessel, water pressure acting on said pressure sensing means is detected thereby and displayed on said pressure indicator to provide a measure of a static force acting on said body extremity; and when said body extremity is positioned in and moved in said water contained in said vessel, water pressure acting on said pressure sensing means is detected thereby and displayed on said pressure indicator to provide a measure of a dynamic force acting on said body extremity.

2. The system for sensing and measuring forces acting on a body extremity as set forth in claim 1,
wherein said first attachment means comprises a first suction cup mounted on said pressure indicator, said first suction cup being configured for enabling a detachable, surface-contacting connection with said component portion, said first suction cup being formed of flexible polymeric material; and second fastener means for detachably securing said first suction cup to said pressure indicator.

3. The system for sensing and measuring forces acting on a body extremity as set forth in claim 2,
wherein said support means comprises a float which is constructed and configured to rest upon a surface portion of said water in said vessel, said float being disc-shaped and formed of polymeric material, said float having an access slot extending therethrough, said access slot extending from the center of said float to a peripheral edge thereof; and
wherein said pressure indicator includes a housing and a pressure gauge mounted on said housing, wherein said housing is formed of polymeric material and is detachably mounted on a planar upper surface of said float in overlying relationship with respect to said access slot by said first fastener means which extends between said housing and said float.

4. The system for sensing and measuring forces acting on a body extremity as set forth in claim 3,
wherein said float further includes a pair of stabilizing fins extending integrally and downwardly from a lower planar surface of said float, said fins extending substantially diametrically across said lower planar surface.

5. The system for sensing and measuring forces acting on a body extremity as set forth in claim 3,
wherein said pressure gauge is mounted on a front wall of said housing, and said first suction cup is mounted on a rear wall of said housing.

6. The system for sensing and measuring forces acting on a body extremity as set forth in claim 3,
wherein said pressure sensing means comprises a load cell which includes a reservoir therein, said reservoir being filled with pressurizing fluid under vacuum; and
wherein said connecting means includes a rigid metal pipe filled with pressurizing fluid and having one end positioned within said housing, said one pipe end being fixed to said pressure gauge, and a flexible tube filled with pressurizing fluid and having a leading end sealingly joined to an opposed end of said metal pipe positioned below said float, and a trailing end sealingly joined to said load cell and said reservoir to form a hydraulic circuit between said pressure gauge and said load cell.

7. The system for sensing and measuring forces acting on a body extremity as set forth in claim 6,
wherein said rigid metal pipe extends downwardly through a bottom wall of said housing and through said access slot of said float.

8. The system for sensing and measuring forces acting on a body extremity as set forth in claim 3,
wherein said second attachment means includes a strap assembly having fixing means for securing said strap assembly on said body extremity, a first patch of adherent material mounted on said strap assembly, a second suction cup formed of flexible polymeric material, and a second patch of adherent material mounted on said second suction cup;
wherein said first and second patches are configured for enabling a detachable, surface-contacting connection with each other; and
wherein said second suction cup is configured for enabling a detachable, surface-contacting connection with said pressure sensing means.

9. The system for sensing and measuring forces acting on a body extremity as set forth in claim 3,
wherein said second attachment means includes a strap assembly having fixing means for securing said strap assembly on said body extremity, a first patch of adherent fabric material mounted on said strap assembly, and a third patch of adherent fabric material mounted on said pressure sensing means; and
wherein said first and third patches are configured for enabling a detachable, surface-containing connection with each other.

10. The system for sensing and measuring forces acting on a body extremity as set forth in claim 1,
wherein said second attachment means includes a strap assembly having fixing means for securing said strap assembly on said body extremity, a first patch of adherent fabric material mounted on said strap assembly, a second suction cup formed of flexible polymeric material, and a second patch of adherent fabric material mounted on said second suction cup;
wherein said first and second patches are configured for enabling a detachable, surface-contacting connection with each other; and
wherein said second suction cup is configured for enabling a detachable, surface-contacting connection with said pressure sensing means.

11. The system for sensing and measuring forces acting on a body extremity as set forth in claim 1,
wherein said second attachment means includes a strap assembly having fixing means for securing said strap assembly on said body extremity, a first patch of adherent fabric material mounted on said strap assembly, and a third patch of adherent fabric material mounted on said pressure sensing means; and wherein said first and third patches are configured for enabling a detachable, surface-contacting connection with each other.

12. The system for sensing and measuring forces acting on a body extremity as set forth in claim 1, wherein said support means comprises a mounting plate for releasably gripping said first fastener means; and wherein said first attachment means comprises a pair of parallel, resilient gripping plates extending orthogonally from said mounting plate for gripping said component element of said water vessel system.

13. The system for sensing and measuring forces acting on a body extremity as set forth in claim 12, wherein said mounting plate includes a planar front surface, a hole centrally positioned in and extending through said mounting plate, and a plug of resilient material mounted in said hole;

wherein said first fastener means includes a first suction cup mounted on said pressure indicator, said first suction cup being configured for enabling a detachable, surface-contacting connection with said planar front surface of said mounting plate in overlying relationship with said hole and said lug of resilient material therein;

wherein said mounting plate, said first suction cup, and said gripping plates are formed of flexible polymeric material; and second fastener means for detachably securing said first suction cup to said pressure indicator.

14. The system for sensing and measuring forces acting on a body extremity as set forth in claim 13, wherein said pressure indicator includes a housing and a pressure gauge mounted on said housing; and wherein said pressure gauge is mounted on a front wall of said housing, and said first suction cup is mounted on a rear wall of said housing.

15. The system for sensing and measuring forces acting on a body extremity as set forth in claim 14, wherein said pressure sensing means comprises a load cell which includes a reservoir therein, said reservoir being filled with pressurizing fluid under vacuum; and wherein said connecting means includes a rigid metal pipe filled with pressurizing fluid and having one end positioned within said housing, said one pipe end being fixed to said pressure gauge, and a flexible tube filled with pressurizing fluid and having a leading end sealingly joined to an opposite end of said metal pipe, and a trailing end sealingly joined to said load cell and said reservoir to form a hydraulic circuit between said pressure gauge and said load cell.

* * * * *